United States Patent [19]

Fretz

[11] Patent Number: 4,730,603
[45] Date of Patent: Mar. 15, 1988

[54] RECEIVER OF AMPLITUDE MODULATED SIGNALS

[75] Inventor: Robert J. Fretz, Maplewood, Minn.

[73] Assignee: Minnesota Mining and Manufacturing Company, St. Paul, Minn.

[21] Appl. No.: 7,986

[22] Filed: Jan. 28, 1987

[51] Int. Cl.$^4$ ............................................. A61B 19/00
[52] U.S. Cl. ..................... 128/1 R; 128/903; 455/337
[58] Field of Search .......... 455/41, 333, 337, 343, 455/203; 329/101, 109, 139; 128/903, 419 C, 419 E

[56] References Cited

U.S. PATENT DOCUMENTS

| | | | |
|---|---|---|---|
| 2,918,573 | 12/1959 | Hollmann | 455/337 |
| 2,934,641 | 4/1960 | Lin | 455/337 |
| 2,941,076 | 6/1960 | Congdon et al. | 455/337 |
| 3,042,872 | 7/1962 | Brahm | 329/101 |
| 3,046,486 | 7/1962 | Rhodes | 455/337 |
| 3,092,779 | 6/1963 | DeNiet | 329/101 |
| 3,357,434 | 12/1967 | Abell | 128/419 E |
| 3,609,556 | 9/1971 | Benson et al. | 455/333 |
| 3,667,477 | 6/1972 | Susset et al. | 128/419 E |
| 3,694,756 | 9/1972 | Carlson | 455/333 |
| 3,796,221 | 3/1974 | Hagfors | 128/419 C |
| 3,999,138 | 12/1976 | Peil et al. | 455/337 |
| 4,403,156 | 9/1983 | Sakamoto | 455/333 |

FOREIGN PATENT DOCUMENTS

| | | | |
|---|---|---|---|
| 911985 | 1/1985 | Japan | 455/333 |
| 197711 | 11/1977 | U.S.S.R. | 455/333 |

Primary Examiner—William E. Kamm
Assistant Examiner—George Manuel
Attorney, Agent, or Firm—Donald M. Sell; James A. Smith; Robert L. Marben

[57] ABSTRACT

An improvement to an implantable amplitude modulated frequency receiver wherein a resistor in the demodulator portion of a prior art receiver, which provides a discharge path for a capacitor, is replaced with an active circuit portion that includes a semiconductor device that provides the discharge path wherein the conductivity level of the semiconductor device is inversely related to the level of conduction of a rectifier to which the received amplitude modulated signal is applied. The active circuit portion improves the efficiency of the receiver in that less power is lost than in the case of the resistor the active circuit portion replaces.

20 Claims, 5 Drawing Figures

RECEIVER OF AMPLITUDE MODULATED SIGNALS

FIELD OF THE INVENTION

The invention presented herein relates generally to systems for electromagnetically transmitting amplitude modulated (AM) signals into the body of a patient and, more particularly, the invention relates to the receiver portion of the system which is implanted in the body.

BACKGROUND OF THE INVENTION

Prior art systems for electromagnetically transmitting amplitude modulated signals into the body of a patient include a transmitter having a tuned circuit which is coupled closely to a tuned circuit provided by the receiver portion of the system that is implanted in the body. FIG. 1 of the drawing is a schematic of a prior art receiver which serves to receive the transmitted AM signal and detect the modulating signal for application to the electrodes which connect with the portion of the body to be stimulated. The prior art receiver of FIG. 1 includes a tuned circuit portion and a demodulator portion. The tuned circuit portion includes a coil 10 and a tuning capacitance, which can be provided by one or more capacitors, and is depicted by the single capacitor 12. The demodulator portion which is connected across the capacitor 12 includes a rectifier that is provided by a semiconductor diode 14 which has its anode connected to one side of the capacitor 12. A resistor 16 and a parallel connected capacitor 18 are connected between the cathode of diode 14 and the other side of the capacitor 12. A capacitor 19 is provided between the cathode of diode 14 and one output conductor 20 for the receiver. Capacitor 19 serves to pass the modulating signal and block the passage of direct current to the output of the demodulator portion. A second output conductor 22 for the receiver is connected to the side of the capacitor 12 that is not connected to the diode 14. An AM signal received by the tuned circuit portion is demodulated by the demodulator portion wherein the AM signal is passed by the diode 14 with capacitor 18 providing decoupling of the carrier portion of the modulated signal. Resistor 16 provides a direct current path to the second output conductor 22 side of the receiver for limited discharge of capacitors 18 and 19 during the time the carrier signal is decreasing in magnitude. A signal which varies in accordance with the modulating signal for the AM signal is thus presented to the load depicted by resistance 21 which is provided by the portion of the body of the patient that is to be connected between the two output conductors 20 and 22.

This prior art receiver is not very efficient in that only about ten percent (10%) of the total power received by a circuit is passed on to the load 21 connected to the two output conductors 20 and 22. The remainder of the power received is dissipated in the resistor 16. In the case of systems using a transmitter that is powered by batteries, it is apparent that an improvement in the efficiency of the prior art receiver is desirable since it will allow the transmitter to be operated at a lower power level for a desired output from the receiver to extend the operating life of the transmitter batteries. Limited improvement can be achieved by selection of the resistance value of the resistor 16 since it must be properly matched to the load impedance. If resistor 16 presents too high a resistance clipping of the waveform occurs and if its resistance is too small, the power loss will be excessive.

SUMMARY OF THE INVENTION

An improved receiver for a system for electromagnetically transmitting amplitude modulated signals into the body of a patient is provided wherein the passive resistor 16 of the prior art circuit of FIG. 1 is replaced by an active circuit portion having an active semiconductor device connected to the rectifier and blocking capacitor for providing a discharge path for limited discharge of the blocking capacitor, the active semiconductor device providing a level of conductivity which is inversely related to the level of conduction of the rectifier, the active circuit portion also having a control circuit connected between the tuned circuit and the active semiconductor device for controlling its conductivity whereby less power is used by the active circuit portion than by the resistor replaced by the active circuit portion to provide a receiver of improved efficiency. The semiconductor device can take the form of a transistor connected in an emitter follower configuration, an operational amplifier connected as a unity gain buffer or it can be a junction field effect transistor.

In one embodiment, a transistor connected as an emitter follower is used in the active circuit portion which replaces the resistor 16 of the prior art circuit of FIG. 1 with a rectifier provided by a diode connected between the base of the transistor and the tuned circuit of the receiver so the base follows the voltage at the emitter of the transistor which is connected to the diode 14. With this arrangement some cross-over distortion occurs at the transition from the time the diode 14 is conducting to when the transistor conducts. Another embodiment, employing a transistor as an emitter follower, avoids this cross-over distortion by the addition of another diode connected in series with the diode connected to the base of the transistor.

BRIEF DESCRIPTION OF THE DRAWINGS

The novel features and advantages of the invention presented herein will become more apparent to those skilled in the art upon consideration of the following detailed description which refers to the drawing, wherein like reference numerals refer to like or similar parts in the circuits schematically shown, and wherein.

DETAILED DESCRIPTION

Figure 1:
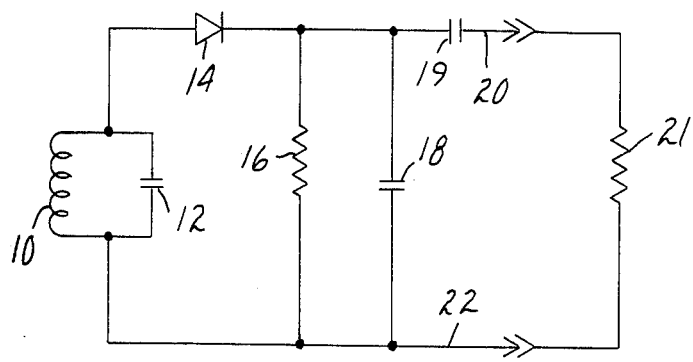
FIG. 1 is a schematic showing of a prior art circuit.
Figure 2:
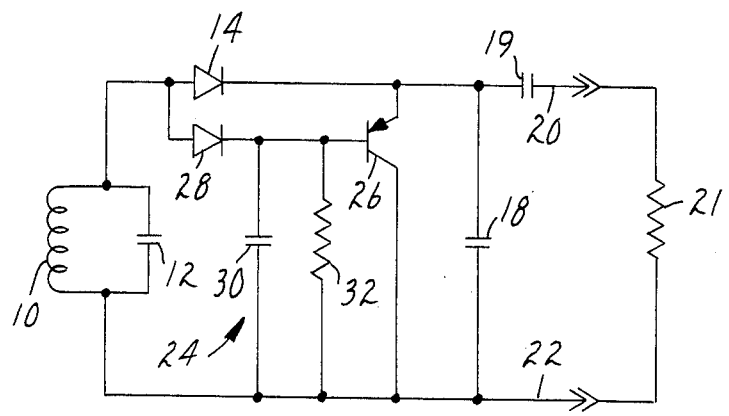
FIG. 2 is a schematic showing of a circuit that is an improvement to the prior art circuit of FIG. 1.

Referring to the circuit shown in FIG. 2, the circuit is like that of the prior art circuit of FIG. 1, which has been described earlier, except that an active circuit portion 24 is used in place of the resistor 16 of the prior art circuit. In the circuit of FIG. 2, the active circuit portion 24 includes an active semiconductor device in the form of a PNP type transistor 26, a diode 28, capacitor 30 and resistor 32. The transistor 26 is connected as an emitter follower wherein its emitter is connected to the connection common to the cathode of diode 14 and capacitors 18 and 19 with its collector electrode connected to the output conductor 22. The diode 28, capacitor 30 and resistor 32 provide a control circuit for the transistor. The base is connected to the tuned circuit and anode of the diode 14 via the diode 28 which has its cathode connected to the base of the transistor 26. The capacitor 30 and resistor 32 are connected in parallel between the base of the transistor and the output conductor 22. The resistor 32 is several times the value of the resistor 16 that is used in the prior art circuit of FIG. 1. Resistor 16 is approximately of the same magnitude as the load connected to the output conductors 19 and 22 or on the order of 3000 ohms. With this arrangement the conductivity level of the transistor 26 will be controlled so it is inversely related to the level of conduction of the diode 14.

When the tuned circuit provided by the coil 10 and capacitance 12 receives an AM signal, portions of the positive half cycles of the modulated radio frequency carrier, for example, 12.0 megahertz, are passed by the diodes 14 and 28. The capacitors 30 and 18 charge to the peak voltage of each positive half cycle of the carrier. The discharge path provided by resistor 32 allows the charge on capacitor 30 to follow the peak voltages of each positive half cycle of the carrier causing the capacitor 30 to present a voltage that is in accordance with the modulating signal used in providing the received AM signal. This results in low conductivity in transistor 26. During portions of the received signal when the positive peak signal decreases in amplitude, diodes 14 and 28 conduct less current causing the voltage at the base of transistor 26 to decrease and the conductivity of transistor 26 to increase. Thus, the conductivity level of the transistor 26 is inversely related to the conduction level of diode 14. Referring to the prior art circuit of FIG. 1, resistor 16 is conducting whenever a signal is received and, therefore, dissipating power. This power loss is reduced by the use of transistor 26 which has reduced conductivity and hence reduced power dissipation or loss during the time that diode 14 is conducting. Resistor 32 also conducts some current and hence dissipates some power, but such power loss is minimal since the magnitude of resistor 32 is several times the value of the resistance used for resistor 16 of the prior art circuit of FIG. 1.

Exemplary components and values for use in the circuit of FIG. 2 for a 12 megahertz AM signal are as follows:
Coil 10—six turns (about 2.5 cm diameter)
Capacitance 12—160 pF
Diodes 14 and 28—Hewlett-Packard HP 5711
Capacitor 18—1000 pF±10%
Capacitor 19—0.12 micro F±10%
Capacitor 30—68 pF±5%
Resistor 32—20,000 ohms±5%
Transistor 26—2N4403

In the case of the circuit as described for FIG. 2, some cross-over distortion will be present at transition between the time diode 14 is conducting to when the transistor 26 is conducting since a difference of about 0.6 volts must be established between the emitter and base of transistor 26 to have it turned on. It is possible to reduce this difference by connecting another diode in series with diode 28 to provide a 0.6 voltage drop with such diode poled in the same direction. With this change it is desirable, though not necessary, to have the transistor biased so it is not so close to the turn on point. This can be accomplished by the addition of a resistor between the emitter of transistor 26 and the cathode of the diode 14. The added resistor should have a value between about 200 to 300 ohms.

Figure 3:
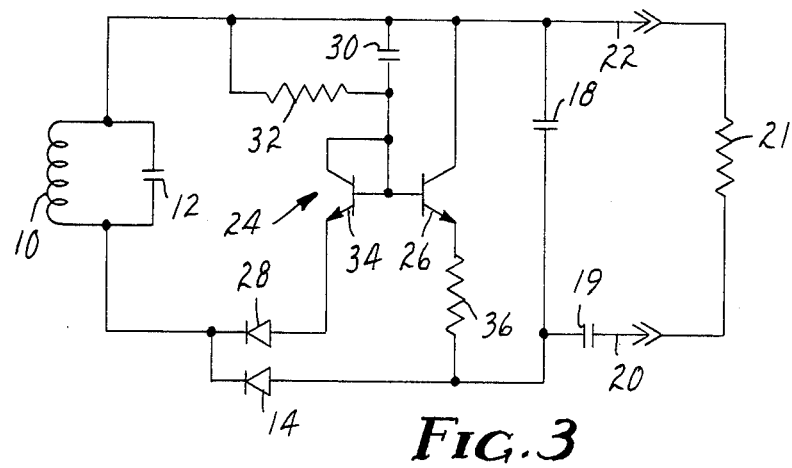
FIG. 3 is a schematic showing of a circuit showing a modification to the circuit of FIG. 2.

The above described modification is illustrated in the circuit shown in FIG. 3, which also serves to illustrate the use of an NPN type transistor instead of a PNP type transistor 26 as shown in FIG. 2. In such case the diodes 14 and 28 of FIG. 3, corresponding to diodes 14 and 28 of FIG. 2 are poled so their cathodes are connected to the tuned circuit provided by the coil 10 and capacitance 12. Since the transistor 26 can be purchased in pairs, a second NPN transistor 34 can be used to provide the additional diode that is indicated can be connected in series with diode 28 to correct the cross-over distortion problem just discussed. This is accomplished by connecting the emitter of transistor 34 to the anode of diode 28 with the base of transistors 26 and 34 connected together and with the base of transistor 34 connected to its collector. The base-emitter of the transistor 34 thus provides the additional diode for connection in series with diode 28. A resistor 36 connected between the emitter of transistor 26 and the output conductor 20 is the resistor which was indicated could be added when employing an additional diode in series with the diode 28 to provide a bias so the transistor is not so close to the turn on point. As in FIG. 2, capacitor 30 connected in parallel with resistor 32 is connected between the base of NPN transistor 26 and output conductor 22.

Exemplary components and values for use in the circuit of FIG. 3 are the same as for the circuit of FIG. 2 except as follows:
Transistors 26 and 34—Type LM394
Resistor 36—260 ohms±5%
Diodes 14 and 28—Hewlett-Packard HP 5082-2837

Figure 4:
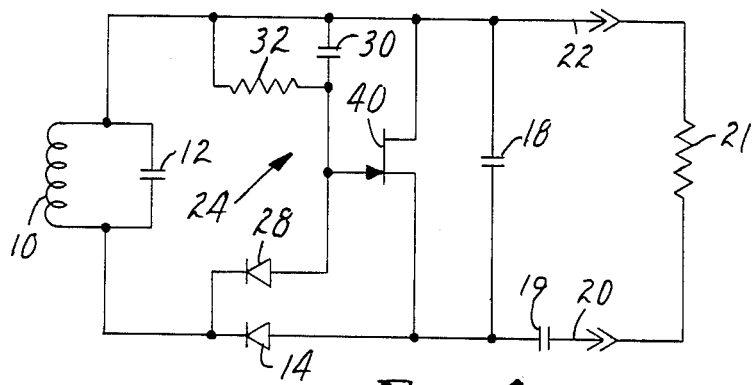
FIG. 4 is a schematic showing of another circuit that is an improvement to the prior art circuit of FIG. 1.

Another circuit embodying the invention is shown in FIG. 4 wherein the active circuit portion 24 used in place of the resistor 16 of the prior art circuit of FIG. 1 includes an N-channel junction field effect transistor (FET) 40, diodes 14, 28, resistor 32 and capacitor 30. The cathodes of diodes 14 and 28 are connected to the tuned circuit provided by the coil 10 and capacitance 12. The anode of diode 28 is connected to the gate electrode of the FET 40 while the anode of diode 14 is connected to the connection common to the capacitors 18 and 19. The resistor 32 and capacitor 30 are connected in parallel with such parallel arrangement connected between the output conductor 22 and the gate electrode of the FET 40. The diode 28, resistor 32 and capacitor 30 form a control circuit for the FET 40. The drain of the FET 40 is also connected to the output conductor 22. The source of FET 40 is connected to the connection common to the anode of diode 14 and capacitors 18 and 19. The capacitor 19 has its side away from the anode of diode 14 connected to the other output conductor 20 which, with conductor 22, provides for connection of the receiver circuit to the load 21 determined by the connections made to the body of a patient. The value of the resistor 32 is much larger than the value of the resistor 16 of the prior art circuit of FIG. 1.

As with the circuits of FIGS. 2 and 3, where the transistor 26 is connected as an emitter follower, the FET 40 is connected as a follower circuit in that the gate and source are both connected to reflect the voltage presented by the received AM signal. With this arrangement the conductivity level of the FET 40 will be controlled so its is inversely related to the level of conduction of the diode 14.

When the tuned circuit provided by the coil 10 and capacitance 12 receives an AM signal, portions of the negative half cycles of the modulated radio frequency carrier, for example, 12.0 megahertz, are passed by the diodes 14 and 28. The capacitors 30 and 18 charge to the peak voltage of each negative half cycle of the carrier. The discharge path provided by resistor 32 allows the charge on capacitor 30 to follow the peak voltages of each negative half cycle of the carrier causing the capacitor 30 to present a voltage that is in accordance with the modulating signal used in providing the received AM signal. This results in low conductivity in FET 40. During portions of the received signal when the negative peak signal decreases in amplitude, diodes 14 and 28 conduct less current causing the voltage at the gate of FET 40 to become less negative and the conductivity of FET 40 to increase. Thus, the conductivity level of the FET 40 is inversely related to the conduction level of diode 14. Referring to the prior art circuit of FIG. 1, resistor 16 is conducting whenever a signal is received and, therefore, dissipating power. This power loss is reduced by the use of FET 40 which has reduced conductivity and hence reduced power dissipation or loss during the time that diode 14 is conducting. Resistor 32 also conducts some current and hence dissipates some power, but such power loss is minimal since the magnitude of resistor 32 is several times the value of the resistance used for resistor 16 of the prior art circuit of FIG. 1.

Exemplary components and values for use in the circuit portion of FIG. 4, which is used in place of the resistor 16 of the prior art circuit of FIG. 1, are as follows:

Field Effect Transistor 40—2N4339
Capacitor 44—33 pF±10%
Diodes 38 and 39—Hewlett-Packard HP 5082-2837

Figure 5:
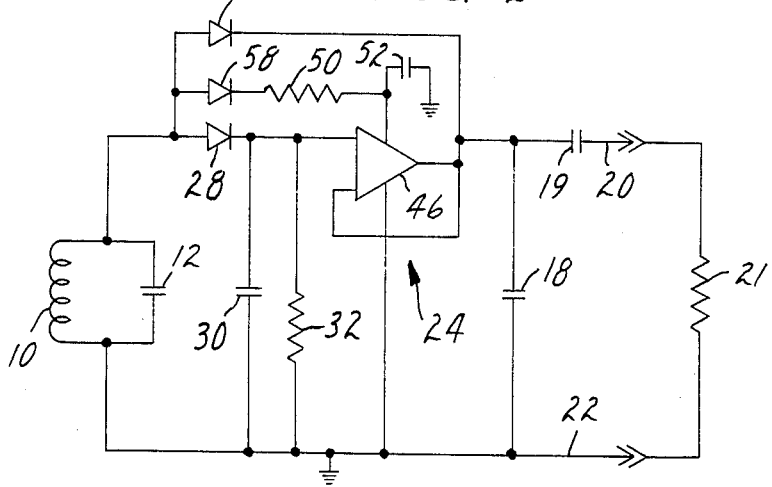
FIG. 5 is a schematic showing of a further circuit that is an improvement to the prior art circuit of FIG. 1.

A further circuit embodying the invention is shown in FIG. 5 wherein the active circuit portion replacing the resistor 16 of the prior art circuit of FIG. 1 includes an operational amplifier 46, resistors 32 and 50, capacitors 30 and 52 and two diodes 28 and 58. The operational amplifier is connected as a follower or unity gain buffer. A circuit including the diode 58, resistor 50 and capacitor 52 serve to provide a positive voltage supply for the operational amplifier 46. The anode of diode 58 is connected to the coil 10 and capacitance 12 while its cathode is connected to the positive power input for the operational amplifier 46 via the resistor 50. The filter capacitor 52 is connected between the operational amplifier 46 side of the resistor 50 and ground. The diode 28, resistor 32 and capacitor 30 provide a control circuit for the operation amplifier 46. The diode 28 has its anode connected to the coil 10 and capacitor 12 with its cathode connected to the positive input of the operational amplifier 46. The capacitor 30 and resistor 32 form a parallel circuit which is connected between the positive input of the operational amplifier 46 and ground which connects to the other side of the coil 10 and to output conductor 22. The negative power input for the operational amplifier 46 is connected to ground. The output of the operational amplifier 46 is connected to the negative input terminal of the operational amplifier and to the connection common to capacitor 18 and the cathode of diode 14. As for the prior art circuit of FIG. 1, the cathode of diode 14 is also connected to one side of capacitor 19. Capacitor 18 has its side away from diode 14 connected to the output or ground conductor 22. The other side of capacitor 19 is connected to the output conductor 20. The output conductors 20 and 22 are used to make connection to a portion of the body of a patient to provide the load for the circuit of FIG. 5. The load is depicted by the resistor 21. With this arrangement the conductivity level of the operational amplifier 46 will be controlled so it is inversely related to the level of conduction of the diode 14.

When the tuned circuit provided by the coil 10 and capacitance 12 receives an AM signal, the positive half cycles of the modulated radio frequency carrier, for example, 12.0 megahertz, are passed by the diodes 14 and 28. The capacitors 30 and 18 charge to the peak voltage of each positive half cycle of the carrier. The discharge path provided by resistor 32 allows the charge on capacitor 30 to follow the peak voltages of each positive half cycle of the carrier causing the capacitor 30 present a voltage that is in accordance with the modulating signal used in provided the received AM signal. This results in low conductivity at the output of the operational amplifier 46. During portions of the received signal when the positive peak signal decreases in amplitude, diodes 14 and 28 conduct less current causing the voltage at the positive input of the operational amplifier 46 to decrease and the conductivity of the operational amplifier to increase. Thus, the conductivity level of the operational amplifier 46 is inversely related to the conduction level of diode 14. Referring to the prior art circuit of FIG. 1, resistor 16 is conducting when a signal is received and, therefore, dissipating power. This power loss is reduced by the use of the operational amplifier 46 which has reduced conductivity and hence reduced power dissipation or loss during the time that diode 14 is conducting. Resistor 32 also conducts some current and hence dissipates some power, but such power loss is minimal since the magnitude of resistor 32 is several times the value of the resistance used for resistor 16 of the prior art circuit of FIG. 1.

Exemplary components and values for use in the circuit of FIG. 5 for a 12 megahertz AM signal are as follows:

Coil 10—six turns (about 2.5 cm diameter)
Capacitance 12—160 pf
Diodes 14, 28 and 60—Hewlett-Packard HP 5711
Capacitor 18—1000 pf±10%
Capacitor 19—1.12 micro F±10%
Capacitor 30—33 pf±10%
Capacitor 52—0.47 micro F±10%
Resistor 32—5000 ohms±10%
Resistor 50—100,000 ohms±10%
Operational Amplifier 46—NE 5230

The particulars of the foregoing description are provided merely for purposes of illustration and are subject to a considerable latitude of modification without departing from the novel teachings disclosed therein. Accordingly, the scope of this invention is intended to be limited only as defined in the appended claims, which should be accorded a bredth of interpretation consistent with this specification.

I claim:

1. An improvement to an implantable amplitude modulated radio frequency receiver having an output adapted for connection to the body of a patient to apply the signal that is used as the modulating signal for an amplitude modulated radio frequency signal received by the receiver which includes a tuned circuit for receiving the amplitude modulated signal and a demodulator circuit portion connected to the tuned circuit for obtaining the modulating signal from the received amplitude modulated radio frequency signal for presentment to the output of the receiver, the demodulator circuit portion including a diode that has its output connected to a blocking capacitor and to a resistor that provides a discharge path for limited discharge of the blocking capacitor, the improvement including an active circuit portion that replaces the resistor, said active circuit portion having an active semiconductor device connected to the diode and blocking capacitor for providing a discharge path for limited discharge of the blocking capacitor, said active semiconductor device providing a level of conductivity which is inversely related to the level of conduction of the rectifier, said active circuit portion having a control circuit connected between the tuned circuit and said active semiconductor device for controlling the conductivity of said active semiconductor device whereby less power is used by said circuit portion than by the resistor replaced by said active circuit portion to provide a receiver of improved efficiency.

2. An improvement to an implantable amplitude modulated radio frequency receiver according to claim 1 wherein said active semiconductor device is a transistor connected as an emitter follower and said control circuit includes a diode connected between the tuned circuit and the base of said transistor.

3. An improvement to an implantable amplitude modulated radio frequency receiver according to claim 2 wherein said control circuit further includes a parallel circuit, including a capacitor and a resistor, connected between the tuned circuit and the base of said transistor.

4. An improvement to an implantable amplitude modulated radio frequency receiver according to claim 1 wherein said active semiconductor device is a transistor connected as an emitter follower and said control circuit includes two series connected diode connected between the tuned circuit and the base of said transistor.

5. An improvement to an implantable amplitude modulated radio frequency receiver according to claim 3 wherein said control circuit further includes a parallel circuit, including a capacitor and a resistor, connected between the tuned circuit and the base of said transistor.

6. An improvement to an implantable amplitude modulated radio frequency receiver according to claim 3 wherein one of said two series connected diodes is provided by the base to emitter junction of a transistor.

7. An improvement to an implantable amplitude modulated radio frequency receiver according to claim 1 wherein said active semiconductor device is a field effect transistor connected as a follower and said control circuit includes a diode connected between the tuned circuit and the gate of the field effect transistor.

8. An improvement to an implantable amplitude modulated radio frequency receiver according to claim 1 wherein said active semiconductor device is an operational amplifier connected as a unity gain buffer and said control circuit includes a diode connected between the tuned circuit and one input of said operational amplifier, said operational amplifier having its output connected to a second input of said operational amplifier and to the output of the diode of the demodulator circuit.

9. An improvement to an implantable amplitude modulated radio frequency receiver according to claim 1 wherein said active semiconductor device is a transistor, field effect transistor or an operational amplifier.

10. An improvement to an implantable amplitude modulated radio frequency receiver according to claim 1 wherein said control circuit includes at least one diode connected between the tuned circuit and said active semiconductor device.

11. An improvement to an implantable amplitude modulated radio frequency receiver according to claim 10 wherein said active semiconductor device is connected as a follower circuit.

12. An improvement to an implantable amplitude modulated radio frequency receiver according to claim 11 wherein said active semiconductor device is a transistor, field effect transistor or an operational amplifier.

13. An improvement to an implantable amplitude modulated radio frequency receiver according to claim 10 wherein said control circuit includes a second diode connected between the tuned circuit and said active semiconductor device.

14. An improvement to an implantable amplitude modulated radio frequency receiver according to claim 10 wherein said control circuit includes a second diode connected in series with said one diode.

15. An improvement to an implantable amplitude modulated radio frequency receiver according to claim 14 wherein said second diode is provided by the base to emitter junction of a transistor.

16. An improvement to an implantable amplitude modulated radio frequency receiver according to claim 1 wherein said active semiconductor device is a transistor and said control circuit includes a diode connected between the tuned circuit and the base of said transistor.

17. An improvement to an implantable amplitude modulated radio frequency receiver according to claim 16 wherein said control circuit further includes a parallel circuit, including a capacitor and a resistor, connected between the tuned circuit and the base of said transistor.

18. An improvement to an implantable amplitude modulated radio frequency receiver according to claim 1 wherein said active semiconductor device is a transistor and said control circuit includes two series connected diodes connected between the tuned circuit and the base of said transistor.

19. An improvement to an implantable amplitude modulated radio frequency receiver according to claim 18 wherein said control circuit further includes a parallel circuit, including a capacitor and a resistor, connected between the tuned circuit and the base of said transistor.

20. An improvement to an implantable amplitude modulated radio frequency receiver according to claim 18 wherein one of said two series connected diodes is provided by the base to emitter junction of a transistor.

* * * * *